(12) United States Patent
Hettrick et al.

(10) Patent No.: US 7,697,987 B2
(45) Date of Patent: Apr. 13, 2010

(54) METHOD AND SYSTEM FOR DETECTING CARDIAC ARRHYTHMIAS DURING OVERDRIVE PACING

(75) Inventors: Douglas A. Hettrick, Blaine, MN (US); Kristin L. Myers, Minneapolis, MN (US); Katherine H. Anderson, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 935 days.

(21) Appl. No.: 11/380,328

(22) Filed: Apr. 26, 2006

(65) Prior Publication Data
US 2007/0255326 A1    Nov. 1, 2007

(51) Int. Cl.
*A61N 1/08* (2006.01)
*A61N 1/365* (2006.01)

(52) U.S. Cl. .............................. 607/14; 607/11; 607/12; 607/17

(58) Field of Classification Search .................. 607/11, 607/12, 14, 17
See application file for complete search history.

(56) References Cited

U.S. PATENT DOCUMENTS

| | | | |
|---|---|---|---|
| 4,712,556 A | 12/1987 | Baker, Jr. | |
| 6,058,328 A | 5/2000 | Levine et al. | |
| 6,353,759 B1 | 3/2002 | Hartley et al. | |
| 6,442,429 B1 * | 8/2002 | Hill et al. | 607/14 |
| 6,941,170 B1 | 9/2005 | Lu | |
| 7,421,294 B2 * | 9/2008 | Chen et al. | 607/14 |
| 2003/0009198 A1 | 1/2003 | Boute | |
| 2003/0088287 A1 * | 5/2003 | Kramer | 607/9 |

FOREIGN PATENT DOCUMENTS

| | | |
|---|---|---|
| WO | WO9961101 | 12/1999 |
| WO | WO0078390 | 12/2000 |
| WO | WO03063961 | 8/2003 |

* cited by examiner

*Primary Examiner*—Carl H. Layno
*Assistant Examiner*—Tammie K. Heller
(74) *Attorney, Agent, or Firm*—Michael C. Soldner

(57) ABSTRACT

A method and apparatus are provided for detecting cardiac arrhythmias during overdrive pacing. A maximum paced rate and a reduced paced rate for a heart are determined, the maximum paced rate being higher than the reduced paced rate. The heart is paced at the maximum paced rate. After the heart is paced at the maximum paced rate for a predetermined amount of time, the heart is paced at the reduced paced rate.

5 Claims, 4 Drawing Sheets

METHOD AND SYSTEM FOR DETECTING CARDIAC ARRHYTHMIAS DURING OVERDRIVE PACING

TECHNICAL FIELD

The present invention generally relates to cardiac pacing methods and systems, and more particularly relates to methods and systems for delivering pacing therapies to treat cardiac arrhythmias.

BACKGROUND

In recent years, the use of implantable cardiac devices, such as pacemakers and defibrillators, has become increasingly common. Such devices are now used not only to treat and terminate cardiac arrhythmias, such as atrial tachycardia (AT) and atrial fibrillation (AF), but to prevent them altogether.

A common pacing made known as "triggered pacing" allows sequential pacing of the lower chambers (i.e., ventricles) when activity is detected in the upper chambers (i.e., atria). One key to the safe application of triggered pacing is the ability of the device to recognize atrial rates that are too fast for safe ventricular pacing. When the atrial activity results from an arrhythmia such as atrial tachycardia, flutter, or fibrillation, instead of normal sinus rhythm, the device may inappropriately pace at very high rates. Therefore, most pacemakers that pace in triggered modes contain a feature known as "mode switching." That is, when an abnormally fast atrial rhythm is detected the device switches out of the triggered pacing mode.

One of the common pacing methods which is used to prevent arrhythmias is known as "overdrive pacing." Overdrive pacing involves sensing a natural pace of the heart and pacing the heart at a slightly increased rate. One particular method, known as Atrial Preference Pacing (APP) is performed by sensing the sinus rate of the heart and pacing the heart, at the atrium, at a rate slightly higher than the sinus rate.

Overdrive pacing, particularly APP, has been relatively successful in preventing arrhythmias. However, it may be difficult for the device to differentiate between sinus pulses and other pathologic cardiac events, such as premature atrial contractions, atrial tachycardia, and atrial flutters and fibrillations, especially when pacing at relatively high rates (e.g., above 100 beats per minute). Therefore, as the sinus rate approaches these high rates, the device may not be able to detect when the patient is experiencing an arrhythmia. As a result, the device may not appropriately switch out of the triggered pacing mode or may not appropriate antiarrhythmia therapy such as anti-tachycardia pacing or atrial defibrillation shocks. Rather, because the device is misidentifying the other cardiac events as sinus pulses, the device may simply further increase the pacing rate.

Accordingly, it is desirable to provide a method for detecting cardiac arrhythmias during overdrive pacing at high rates. In addition, it is desirable to provide a cardiac device capable of detecting arrhythmias during such pacing. Furthermore, other desirable features and characteristics of the present invention will become apparent from the subsequent detailed description and the appended claims, taken in conjunction with the accompanying drawings and the foregoing technical field and background.

BRIEF SUMMARY

A method is provided for detecting a cardiac arrhythmia during overdrive pacing. The method comprises determining a maximum paced rate and a reduced paced rate for a heart, the maximum paced rate being higher than the reduced paced rate, pacing the heart at the maximum paced rate, and after pacing the heart at the maximum paced rate for a predetermined amount of time, pacing the heart at the reduced paced rate.

An apparatus is provided for detecting a cardiac arrhythmia during overdrive pacing. The apparatus comprises a housing, a sense amplifier within the housing and responsive to depolarizations of a chamber of a heart, a pulse generator within the housing to produce cardiac stimulation pulses to the heart, a controller within the housing and coupled to the sense amplifier and the pulse generator. The controller is configured to set a maximum paced rate and a reduced paced rate for a heart, the maximum paced rate being higher than the reduced paced rate, pace the heart at the maximum paced rate, and after pacing the heart at the maximum paced rate for a predetermined amount of time, pace the heart at the reduced rate.

BRIEF DESCRIPTION OF THE DRAWINGS

The present invention will hereinafter be described in conjunction with the following drawing figures, wherein like numerals denote like elements.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description. It should also be understood that FIGS. 1-4 are merely illustrative and may not be drawn to scale.

FIG. 1 through FIG. 4 illustrate an implantable cardiac device and a method for detecting and treating cardiac arrhythmias using the cardiac device. A maximum paced rate and a reduced paced rate for a heart are determined. The heart is then paced using anti-tachyarrhythmia pacing or overdrive pacing. In one embodiment, the overdrive pacing is Atrial Preference Pacing (APP), in which a sinus rate, or atrial rate, of the heart is detected, and the heart is paced at a preferred rate (or overdrive rate) that is just above the sinus rate. If the overdrive pacing paces the heart at the maximum paced rate for a predetermined amount of time, or for a predetermined number of consecutive beats, the device slows the pacing of the heart to the reduced rate. With the pacing at the reduced rate, the presence of an arrhythmia may be detected. If an arrhythmia is detected, the device employs an appropriate therapy to eliminate the arrhythmia or switches to an appropriate non tracking pacing mode. If an arrhythmia is not detected, the overdrive pacing continues and the pacing again appropriately increases to a rate that corresponds to the sinus rate.

Figure 1:
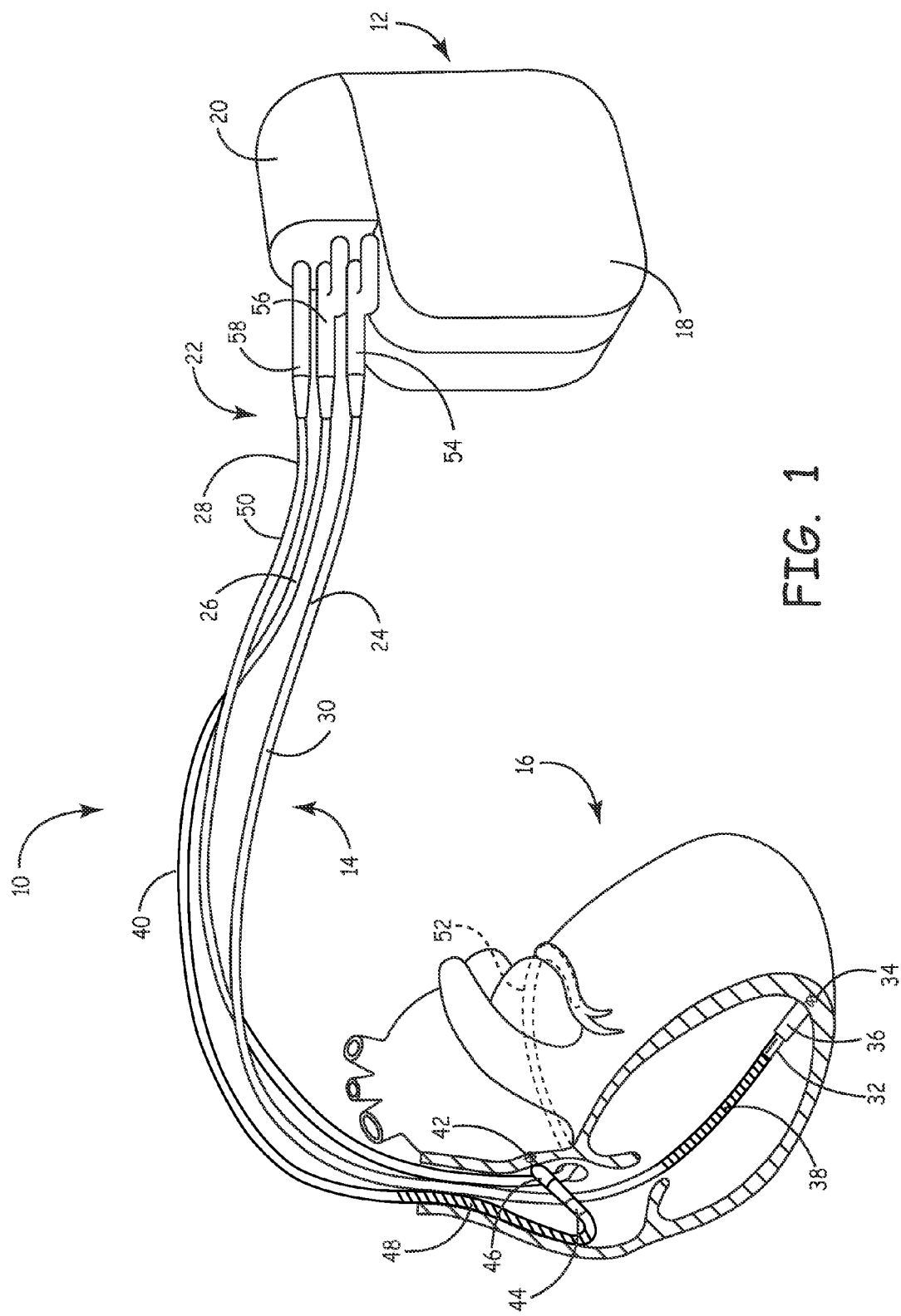
FIG. 1 is an isometric view of a cardiac treatment system, including an implantable cardiac device and a lead set.

FIG. 1 illustrates a cardiac treatment system 10 according to one embodiment of the present invention. The system 10 includes an implantable cardiac device 12 and a lead set 14, which is connected to a heart 16. The implantable cardiac device 12 includes a housing 18, a connector block 20, and lead connector assemblies 22. The implantable cardiac device 12 may be a pacemaker, cardioverter, and/or defibrillator, as is commonly understood in the art. Although not illustrated in detail, an uninsulated portion of the housing 18 may function as a subcutaneous defibrillation electrode to defibrillate either the atria or ventricles of the heart.

The lead set 14 includes a ventricular lead 24, an atrial/ superior vena cava (SVC) lead 26, and a coronary sinus lead 28. The ventricular lead 24 includes an elongated insulative lead body 30 that carries three concentric coiled conductors, separated from one another by tabular insulative sheaths. The ventricular lead 24 also includes a ring electrode 32, an extendable helix electrode 34, mounted retractably within an insulative electrode head 36, and an elongated coil electrode 38 connected at a distal end thereof. Although not specifically illustrated, the electrodes 32, 34, 36, and 38 are each coupled to one of the coiled conductors within lead body 30 and can be used for both cardiac pacing and sensing of ventricular depolarizations.

The atrial/SVC lead 26 includes an elongated insulative lead body 40, similar to lead body 30, carrying three concentric coiled conductors, separated from one another by tubular insulative sheaths. The atrial/SVC lead 26 also includes a ring electrode 42 and an extendable helix electrode 44, mounted retractably within an insulative electrode head 36, connected at a J-shaped distal end thereof. The electrodes 32, 34, and 36 are each coupled to one of the coiled conductors within lead body 40 and are employed for atrial pacing and for sensing atrial depolarizations. An elongated coil electrode 48 is provided proximal to ring electrode 32 and coupled to the third conductor within lead body 30.

A coronary sinus lead 28 includes an elongated insulative lead body 50 that carries one coiled conductor and an elongated defibrillation electrode 46 coupled to the conductor at a distal end thereof. The defibrillation electrode 46 is located within the coronary sinus and great vein of the heart 16.

The lead connector assemblies 22 include a ventricular lead connector 54, an atrial/SVC lead connector 56, and a coronary sinus lead connector 58. The ventricular lead connector 54 and the atrial/SVC lead connector 56 are bifurcated and carry three electrical connectors, each coupled to a respective conductor within the ventricular lead connector 54 and the atrial/SVC lead connector 56. The coronary sinus lead connector 58 carries an electrical connector that is coupled to the coiled conductor within the lead body 50 of the coronary sinus lead 28. The leads 24, 26, and 28 are fed through the lead connectors 54, 56, and 58, pass through the connector block 20, and into the housing 18.

Figure 2:
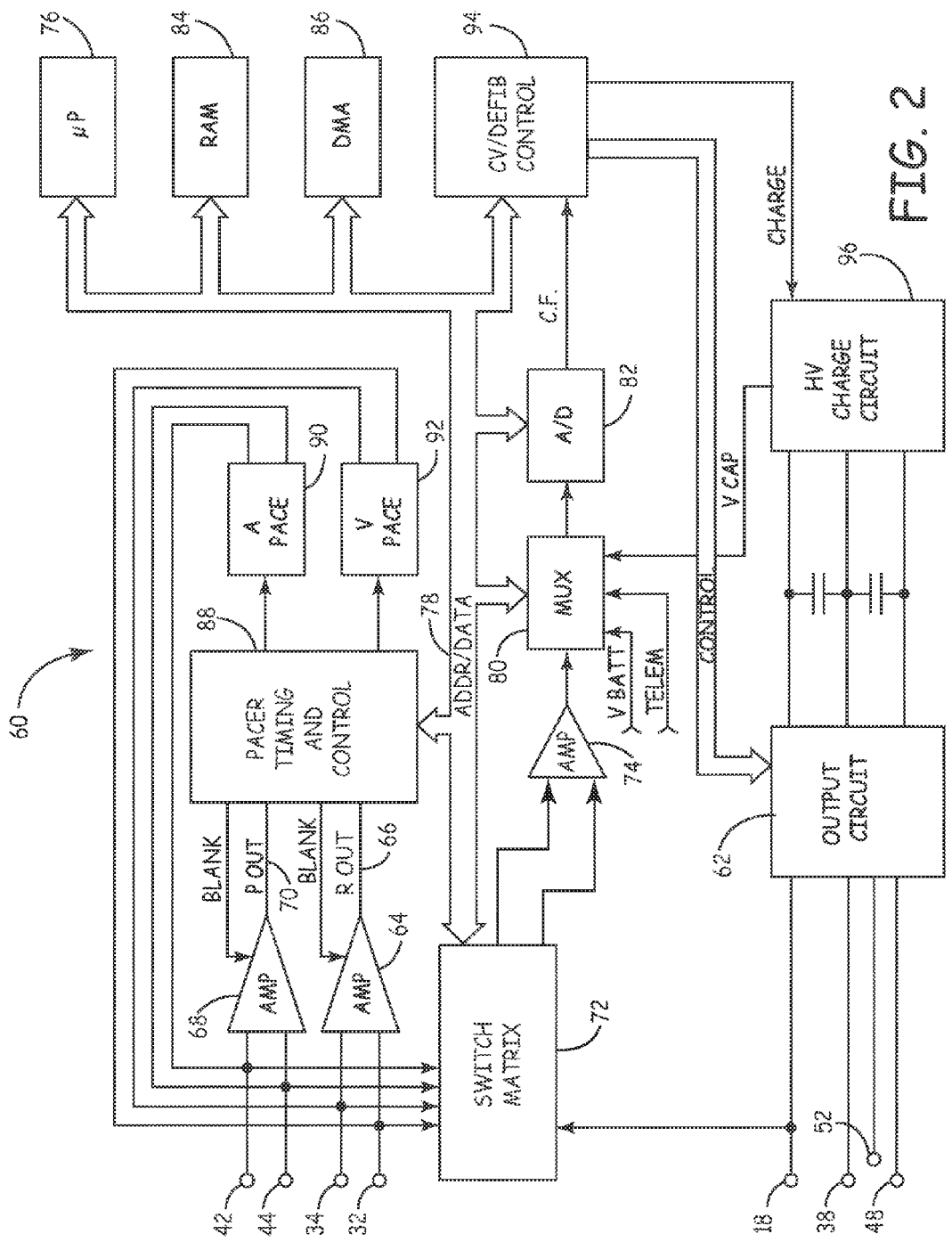
FIG. 2 is a block diagram of a system within the implantable cardiac device illustrated in FIG. 1.

FIG. 2 is a functional block diagram illustrating a system 60 capable of performing the methods of detecting cardiac arrhythmias according to one embodiment of the present invention. The system 60 may be implemented within device 12 of FIG. 1, and may take the form of an implantable device that integrates various pacemaker/cardioverter/defibrillator functions. FIGS. 1 and 2 are exemplary of the type of device in which the invention may be embodied, as the invention may be practiced in a wide variety of device implementations, including devices providing therapies for treating atrial arrhythmias or both atrial and ventricular arrhythmias. In addition, the invention may be practiced in pacemakers that do not provide cardioversion or defibrillation, as well as devices that deliver different forms of antiarrhythmia therapies such as nerve stimulation or drug administration.

In the example illustrated in FIG. 2, electrodes 32, 34, 38, 42, 44, 48 and 52 represent the electrodes designated by similar reference numerals shown in FIG. 1. Likewise, electrode 18 represents the uninsulated portion of the housing 18 of device 10, as illustrated in FIG. 1, which may function as a defibrillation electrode. Referring again to FIG. 2, electrodes 18, 38, 48, and 52 are coupled to a high voltage output circuit 62 (e.g., pulse generator). Electrodes 32 and 34 are coupled to an R-wave amplifier 64, which preferably takes the form of an automatic gain controlled amplifier providing an adjustable sensing threshold as a function of the measured R-wave amplitude. A signal is generated on an R-out line 66 whenever the signal sensed between electrodes 32 and 34 exceeds the present sensing threshold.

Electrodes 42 and 44 are coupled to a P-wave amplifier 68, which also may take the form of an automatic gain controlled amplifier providing an adjustable sensing threshold as a function of the measured R-wave amplitude. A signal is generated on a P-out line 70 when the signal sensed between electrodes 42 and 44 exceeds the sensing threshold. A switch matrix 72 selects which of the available electrodes are coupled to a wide band amplifier 74 for use in digital signal analysis. The selection of which of the electrodes are to be operated is controlled by a controller, which may take the form of a microprocessor 76. The microprocessor 76 controls selection of the electrodes via the switch matrix 72 through a data/address bus 78. Signals from the electrodes selected for coupling to the wide band amplifier 74 are provided to a multiplexer 80 and thereafter converted to multi-bit digital signals by an analog-to-digital (A/D) converter 82, for storage in a random access memory (RAM) 84 under control of a direct memory access (DMA) circuit 86.

The microprocessor 76 may preferably employ digital signal analysis techniques to characterize the digitized signals stored in the random access memory 84 to recognize and classify the heart rhythm (e.g., arrhythmia) using any of a variety of known signal processing methods. In particular, the microprocessor 76 may implement a detector that monitors the cycle length and regularity of the heart rhythm during an AT episode. The remainder of the circuitry illustrated in FIG. 2, such as pacer timing and control circuitry 88, output circuits 90 and 92, cardioversion/defibrillation control circuitry 92, and high voltage charging circuit 94, is dedicated to the provision of cardiac pacing, cardioversion, and defibrillation therapies. The microprocessor 76 is programmed to control the circuitry of FIG. 2 to deliver various pacing therapies and detect different heart rhythms for selection of pacing therapy sequences to be applied to the heart.

Although not specifically illustrated, it should be understood that the system 60, either as hardware or instructions stored, for example, within the microprocessor 76, the random access memory 84, and/or pacing timing and control circuitry 88, also includes predetermined maximum and reduced pacing rates, both of which are adjustable by a user (e.g., a doctor) of the system 10 illustrated in FIG. 1. As will be appreciated by one skilled in the art, the maximum pacing (or "paced") rate is the highest rate at which the device 12 will pace the heart 16. The maximum paced rate may be, for example, between 100 and 140 beats per minute, such as 120 beats per minute, and the reduced paced rate may be, for example, between 60 and 80 beats per minute, such as 70 beats per minute. The system 60 may also include a maximum rate pacing counter flag to signal when the maximum paced rate has been achieved and a maximum rate pacing counter to count the number of cardiac events (e.g., beats) that occur while the maximum rate pacing counter flag is set.

In use, referring again to FIG. 1, the system 60 may apply anti-tachyarrhythmia pacing or overdrive pacing to the heart 12. In one embodiment, the anti-tachyarrhythmia pacing is APP and is applied to an atrium of the heart 12. However, it should be understood that the other types of pacing may be used as well. As will be appreciated by one skilled in the art, the device 10 senses the sinus rate of the heart and, in accordance with APP, delivers atrial pacing pulses at a rate just above the sinus rate.

Figure 3:
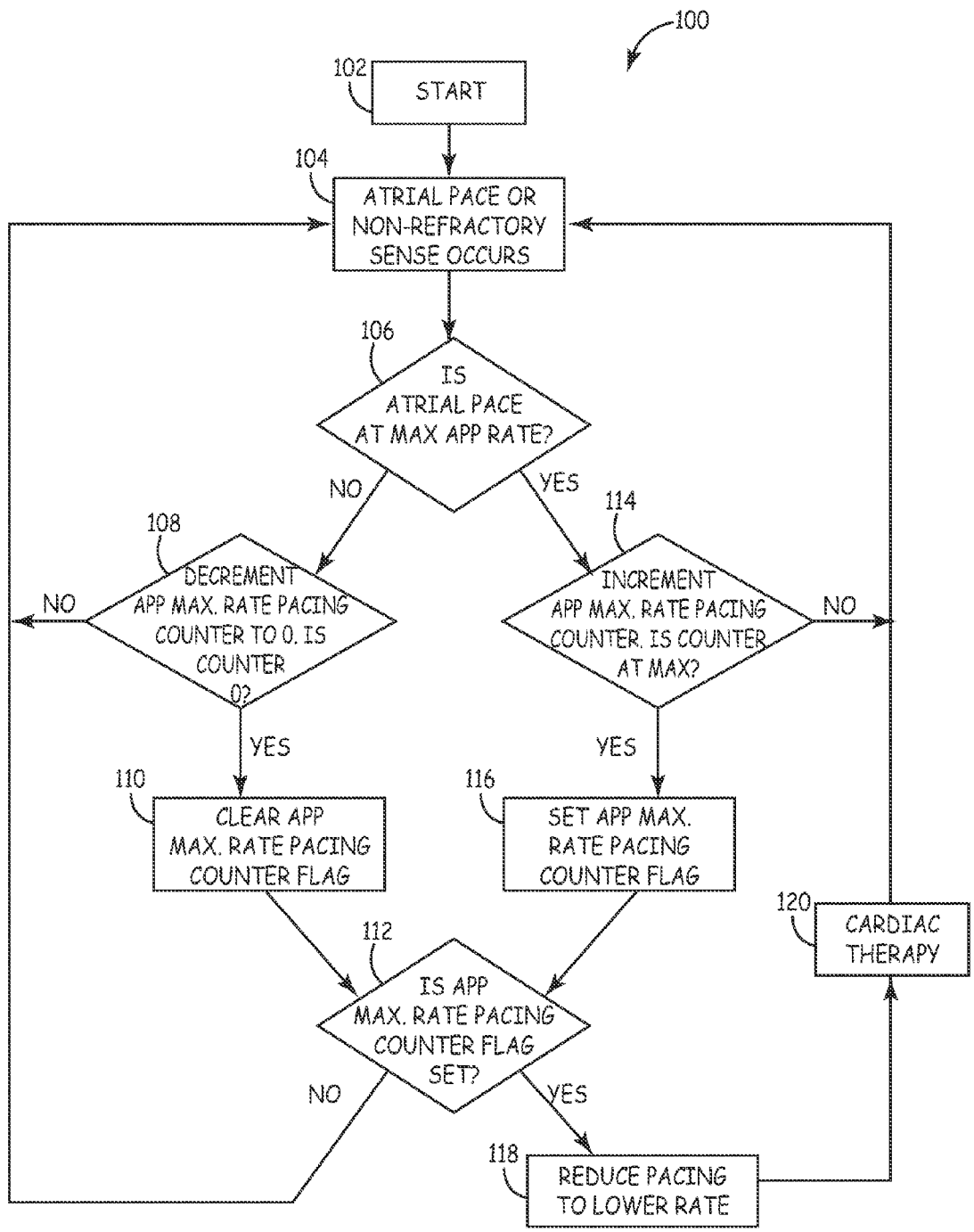
FIG. 3 is a flow chart of a method for detecting cardiac arrhythmias during overdrive pacing according to one embodiment of the present invention.

FIG. 3 illustrates a method 100 for detecting cardiac arrhythmias during overdrive pacing according to one embodiment of the present invention. At step 102, the overdrive pacing is begun, and at step 104 either an atrial pace or a non-refractory sense occurs and is detected. In one embodiment, in accordance with APP, the sinus rate of the heart is sensed or detected, and the heart is then paced at a rate just above the sinus rate. As will be appreciated by one skilled in the art, the actual rate sensed may be the atrial rate, which could be the sinus rate of the heart or the result of an atrial tachyarrhythmia.

At step 106, it is determined whether or not the atrial pacing is at the predetermined APP maximum rate. If the atrial pacing is not at the maximum rate, the process continues to step 108, where the maximum rate pacing counter is decremented and set (or re-set) to 0. Then at step 110, the maximum rate pacing counter flag is cleared (i.e., "turned off"). Next, at step 112, it is determined whether or not the maximum rate pacing counter flag is set. If the flag is not set, the process returns directly to step 104.

In accordance with APP, if the sinus rate of the heart increases, the device 12 will increase the pacing rate to stay ahead of the sinus rate and continue overdrive pacing. Returning to step 106, if the atrial pacing reaches the maximum rate, the method 100 proceeds to step 114 where the maximum rate pacing counter is incremented (i.e., increased by 1). The determination is then made as to whether the maximum rate pacing counter is at its maximum (e.g., 256). If the counter is not at the maximum, the process returns to step 104. If the counter is at the maximum, the process continues to step 116 where the maximum rate pacing counter flag is set (i.e., "turned on").

The process then continues again to step 112, and if the maximum rate pacing counter flag is set, the process moves to step 118. At step 118, the pacing rate is reduced to the lower rate, or reduced rate. As will be appreciated by one skilled in the art, after the pacing is brought down to the lower rate, the device 10 will be able to determine whether or not an arrhythmia is present in the heart by employing known techniques. If an arrhythmia is detected, the device 10 may, at step 120, employ a pacing therapy sequence or switch to a different pacing mode, as is commonly understood in the art. If an arrhythmia is not detected, the device continues to pace the heart using APP and the pacing rate of the heart is increased to be slightly higher than the sinus rate of the heart.

Therefore, if the maximum paced rate is set to 120 beats per minute, the maximum rate pacing counter flag is set after just over 2 minutes of constant pacing (i.e., the time it takes for the heart to beat 256 times when being paced at 120 beats per minute) at the maximum rate. At that time, the pacing of the heart is reduced to the lower rate (e.g., 70 beats per minute). As will be appreciated by one skilled in the art, the lower rate allows the device 12 to detect whether or not the heart is experiencing an arrhythmia.

It should be understood that other criteria, besides a consecutive number of beats, may be used to trigger the reduction of the pacing rate. The maximum rate pacing counter flag may also be set by pacing at the maximum rate for a predetermined percentage of a predetermined total amount of beats. For example, the percentage may be set to 95% of a 270 beat period. In such a case, if at any time the heart is paced at the maximum rate for 256 (or more) out of 270 beats, the maximum rate pacing counter will be set and the pacing rate will be reduced as described above. As another example, a predetermined number of beats at the maximum rate within any period of time may trigger the reduction. In such a case, if the predetermined number of beats is set to 2000 beats, and the heart is paced at the maximum rate for 2000 beats over even an extended period of time (e.g., a period of several weeks), the pacing rate would be reduced as described above.

Figure 4:
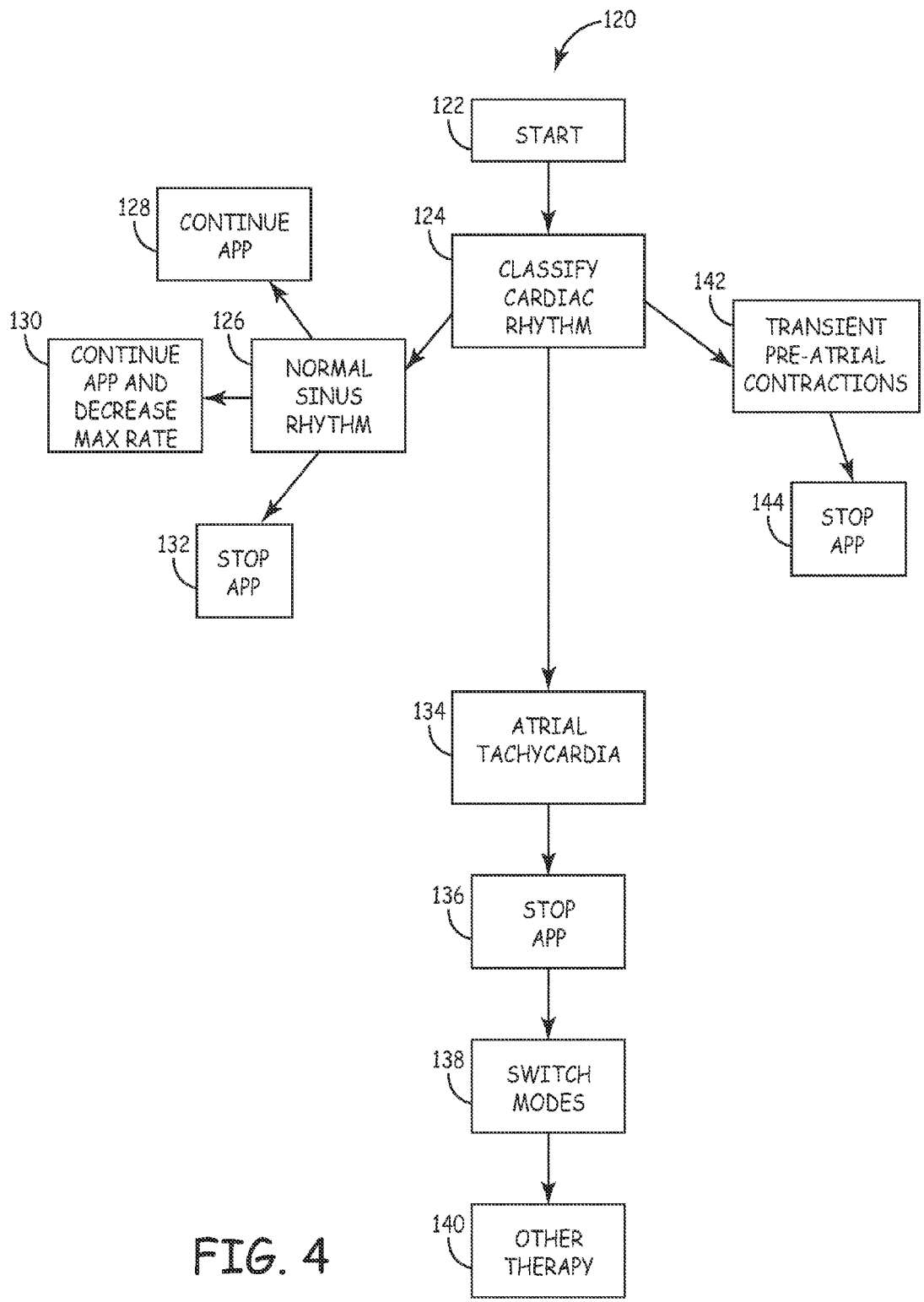
FIG. 4 is a flow chart of a method for treating cardiac arrhythmias.

FIG. 4 illustrates a cardiac therapy method 120, as indicated at step 120 in FIG. 3, according to one embodiment of the present invention. At step 122, the method begins with the pacing rate of the heart being reduced to the lower rate as described above. At step 124, the rhythm of the heart is classified employing known techniques. If the rhythm is determined to be a normal sinus rhythm, the method proceeds to step 126. At step 126, the next appropriate step is determined, as will be appreciated by one skilled in the art. In one embodiment, three possibilities for continuing treatment of the heart are continuing APP (step 128), continuing APP and decreasing the maximum rate (step 130), and ceasing APP (step 132).

Still referring to FIG. 4, if at step 124 the cardiac rhythm is determined to be an atrial tachycardia, the process continues to block 134. In one embodiment, at step 136, APP is then ceased. As shown, at step 138, if appropriate, mode switching may then occur. As is commonly understood, the mode switching may include switching from a tracking pacing therapy to a non-tracking therapy. Additionally, at step 140, other therapies, such as further pacing therapies and electric shocks may also be applied, if appropriate.

If at step 124, the cardiac rhythm is determined to consist of transient (or intermittent) pre-atrial contractions, as is commonly understood, the process continues to step 142. As shown, in one embodiment, APP is then stopped at step 144. It should be understood that the therapy method illustrated in FIG. 4 is intended as an example, as other treatment methods may also be used.

One advantage of the system and method described above is that because the pacing of the heart is reduced from the maximum rate, it is possible to detect whether or not the heart is experiencing an arrhythmia. Therefore, the effectiveness with which the system treats patients is increased.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A method for detecting a cardiac arrhythmia during pacing comprising:
    determining a maximum paced rate and a reduced paced rate for a heart, the maximum paced rate being higher than the reduced paced rate;
    sensing a sinus rate of the heart;
    pacing the heart at a preferred rate, the preferred rate being greater than the sinus rate, wherein pacing the heart at the preferred rate comprises adjusting the preferred rate based on sensing of the sinus rate during pacing at the preferred rate;

detecting that, due to the adjustment of the preferred rate, the preferred rate equals the maximum paced rate for a predetermined amount of time; and pacing the heart at the reduced paced rate in response to detecting that the preferred rate equals the maximum paced rate for a predetermined amount of time.

2. The method of claim 1, wherein pacing the heart at the reduced paced rate in response to detecting that the preferred rate equals the maximum paced rate for a predetermined amount of time comprises pacing the heart at the reduced paced rate if the preferred rate equals the maximum paced rate for a predetermined number of consecutive cardiac events or if the preferred rate equals the maximum paced rate for a predetermined percentage of a predetermined total number of cardiac events.

3. The method of claim 2, further comprising performing an arrhythmia detection method on the heart during said pacing of the heart at the reduced paced rate.

4. The method of claim 3, wherein the maximum paced rate is between 100 and 140 beats per minute and the reduced paced rate is between 60 and 80 beats per minute.

5. The method of claim 3, wherein said pacing comprises Atrial Preference Pacing (APP).

* * * * *